US00PP15049P2

(12) United States Plant Patent
Kochi

(10) Patent No.: US PP15,049 P2
(45) Date of Patent: Jul. 27, 2004

(54) ALMOND TREE NAMED 'KOCHI'

(50) Latin Name: *Prunus dulcis*
Varietal Denomination: Kochi

(75) Inventor: Mark Kochi, Yuba City, CA (US)

(73) Assignee: Sierra Gold Nurseries, Yuba City, CA (US)

( * ) Notice: Subject to any disclaimer, the term of this patent is extended or adjusted under 35 U.S.C. 154(b) by 0 days.

(21) Appl. No.: 10/377,937

(22) Filed: Feb. 28, 2003

(51) Int. Cl.[7] ..... A01H 5/00

(52) U.S. Cl. ..... Plt./155

(58) Field of Search ..... Plt./155

*Primary Examiner*—Anne Marie Grunberg
*Assistant Examiner*—S B McCormick-Ewoldt
(74) *Attorney, Agent, or Firm*—Mark D. Miller

(57) ABSTRACT

A new and distinct variety of almond tree which is somewhat similar to 'Nonpareil' (non patented) but distinguished therefrom by producing nuts that mature a week before 'Nonpareil' for harvesting, husking, shelling, and shipping, which further produces a high quality nut of medium size with a good shell. This new invention has a sweet flavor and is comparatively free of doubled kernels in the shell.

1 Drawing Sheet

BACKGROUND OF THE NEW VARIETY

The present invention relates to a new and distinct variety of almond tree, *Prunus dulcis,* which will hereinafter be denominated varietally as 'Kochi' and more particularly to an almond tree which produces fruit for commercial harvesting, hulling, shelling and shipping during the third week of August (Aug. 15–20th) in the Yuba City area of the Sacramento Valley of Northern California and which is further distinguished by producing a soft shelled almond, the kernel having a flavor characteristic that is excellent.

There are a number of criteria of which a commercial variety of tree fruits and nuts must excel in order to be commercially successful, such as ripening date, flavor, texture, storage ability as well as shipping quality. With tree fruits as well as nuts such as almonds the early ripening date, the quality of the meat of the kernel, freedom from unusual number of doubles, as well as the soft shell of the present almond makes it commercially attractive with a substantial likelihood of success.

Almond varieties in particular are characterized as to soft shell or hard shell, the latter characteristic making kernel removal and marketing more difficult. Most particularly in almond varieties of tree fruits and nuts, the ease of shelling and the high quality of the kernel plus a very low percentage of doubles (confirmed by Blue Diamond Growers in December, 2001 at 0.54 of 1%) gives the present almond an excellent appeal to the distributor and consumer.

ORIGIN AND ASEXUAL REPRODUCTION OF THE NEW VARIETY

The present invention of almond tree was discovered by the inventor in 1994 as a volunteer seedling approximately ¼ mile from a 'Drake' almond orchard on Carlson Road several miles south of Yuba City, Calif.

After several years of observation the inventor had the new invention asexually propagated on Nemaguard and Lovell peach tree rootstocks at the Sierra Gold Nursery located at 5320 Garden Hwy, Yuba City, Calif. in 1997. These trees have been observed over the past five years and the kernels observed and analyzed during the past two years.

The trees have been observed by the inventor, as well as nursery and university personnel and have continued to be identical to the original tree of the new variety. A total of 50 trees were planted in four orchards throughout the almond growing areas of California outside of this growing site and have confirmed the identical characteristics by above named personnel. The trees are in their 4th leaf and the vigor of this new variety is similar to the vigor of the 'Nonpareil.'

SUMMARY OF THE NEW VARIETY

The present 'Kochi' almond tree is characterized by producing a soft shelled, well sealed almond which resembles the 'Nonpareil' almond. The fruit (nut in this case) produced by the 'Kochi' almond is ripe (mature) for commercial harvesting, hulling, shelling and shipping in the third week of August (Aug. 15–20). The new and novel variety, as stated earlier, is probably more similar to the 'Nonpareil' but distinguishes itself by harvesting a week before 'Nonpareil' with a high quality and high percentage of meat. The meat weight is 55.1% of the total weight of the almond in the shell. The low percentage of doubles in the shell (0.54%) is an excellent characteristic. Although this new invention resembles the 'Nonpareil,' the meat quality is sweeter and slightly darker.

BRIEF DESCRIPTION OF THE DRAWING

The drawing is a colored photograph showing the mature fruit (nuts in this case) of the new variety of almond tree of the present invention with the following details: the upper left view shows a splitting husk on a nut; the upper central view shows leaves and branches; the view below and to the left of the leaves displays the shelled nut with the suture up (next to a tie-pin for scale); the view below and to the right of the leaves shows the inside of the unshelled nut (kernel) to display the shape of the nut (the central nut next to a tie-pin for scale); directly below the leaves is a row of three nuts displaying the nuts in side views without the husks (the shells); and finally the lowermost view shows the fruit (in the hull) attached to the young branch or twig, and young terminal branches.

DETAILED DESCRIPTION

Referring more specifically to the pomological details of this new and distinct variety of almond tree, the following has been observed under the ecological condition prevailing at the designated orchard of origin near Yuba City, Calif. All major color code designations are by reference to the Diction of Color by Maerz & Paul, First Edition, published in 1930. Common color names are also occasionally used.

TREE

Generally:

1. *Origin.*—Open pollinated volunteer seedling — found growing about ¼ mile from a 'Drake' planting.
2. *Vigor.*—Vigorous and hardy.
3. *Chilling.*—Under Northern California Sacramento Valley conditions; normal chilling requirement.
4. *Figure.*—Spreading and upright growth crotch angles vary 45–60%; height 10–12 ft; width 8–10 ft.
5. *Productive.*—Very productive at 5th leaf.
6. *Regularity of bearing.*—Regular.

Trunk:

1. *Size.*—Moderate, 15¾ inches to 19 inches in circumference 16–19 inches above ground.
2. *Surface texture.*—Rough.
3. *Color code.*—Hematite Red (7-H-3).
4. *Lenticels.*—More than 20 between twigs and branches. Size — large 4–6 mm (0.16–0.24 inch).

Branches:

1. *Size.*—Moderate — 8 inch circumference, 35 inches above ground level, angle at branches at crotch 45–60°.
2. *Surface texture.*—Mature — slightly rough. Immature — smooth.
3. *Color code.*—(One year or older) near Mauve Taupe, Copra (7-E-8). Immature — Apple green (19-J-6).
4. *Lenticels.*—On immature branches, none observed. On mature branches, 2–3 per inch.

Leaves:

1. *Foliage.*—Medium size — typical for almond.
2. *Size.*—Length: 60–105 mm (2.637–4.13 inch). Width: 23–27 mm (0.90–1.06 inch).
3. *Shape.*—Lanceolate.
4. *Thickness.*—Normal for almond.
5. *Color code.*—Upwardly disposed surface — Brunswick Gr. Lt.$^{P}$ (22-L-10). Downwardly disposed surface — Garland green (22-H-7).
6. *Marginal form.*—Crenulate.
7. *Leaf vein.*—Color Code — Lettuce green (20-L-5). Thickness — 1 mm (0.039 inch). Pattern — pinnate.
8. *Leaf glands.*—0–3 reniform.
9. *Petiole.*—Length: 23–26 mm (0.90–1.417 inch). Thickness: 1½ mm (0.059 inch). Color Code — Lettuce green (20-L-5).
10. *Petiolar sinus.*—Rounded base.
11. *Stipules.*—None.
12. *Arrangement.*—Opposite.

FLOWERS

1. *Date of bloom.*—Feb. 26 — 75%.
2. *Bloom amount.*—Heavy in clusters of 3–4.
3. *Color.*—Very light pink (1-B-1).
4. *Petals.*—Diameter of buds: 5–7 mm (0.2–0.28 inch). Color Code bud tips — Light pink (1-C-1).
5. *Diameter of bloom.*—32–40 mm (1.26–1.57 inch).
6. *Margin of petals.*—Undulated with apex notching.
7. *Petals.*—10–12 mm (0.39–0.472 inches) width 15–17 mm (0.59–0.67 inches) length.
8. *Sepals.*—5 in number (in calyx). Color Code — Ambrosia (7-H-5); at base near Eden green (20-C-10).
9. *Pistil.*—1, 12–14 mm (0.472–0.55 inch) length. Color — Grape green (21-J-1).
10. *Anthers.*—Small, 1 mm (0.039 in). Color — Butterscotch (14-F-9).
11. *Stamens.*—14–16 per bloom, 8–10 mm (0.315–0.39 inch) long; Color — Ambrosia (7-H-5).
12. *Pedicel.*—Short. Length: 3 mm (0.12 inch). Width: 2 mm (0.078 inch).
13. *Bud.*—Diameter: 5–7 mm (0.2–0.28 inch). Length: 4–5 mm (0.16–0.2 inch).

CROP

1. *Productivity.*—Very good for 4th leaf.
2. *Harvest period.*—Aug. 15–20.
3. *Distribution on tree.*—Well distributed throughout.
4. *Tenacity.*—Good.

Hull (outer):

1. *Texture.*—Slightly pubescent.
2. *Pits.*—None.
3. *Form.*—Ovate.
4. *Thickness.*—15–17 mm (0.59–0.67 inch).
5. *Flesh.*—None.
6. *Suture.*—Minimal.
7. *Color.*—Chinchilla (37-A-3).
8. *Dehiscence.*—Good.
9. *Splitting.*—Good.

Nut (shell):

1. *Size.*—Length: 38–44 mm (1.50–1.75 inch). Width: 22–26 mm (0.866–1.02 inch). Thickness: 12–15 mm (0.472–0.59 inch).
2. *Form.*—Ovate.
3. *Thickness.*—12–15 mm (0.472–0.59 inch).
4. *Shell.*—Outer shell — flake. Inner shell — brittle.
5. *Color.*—Tinsel deep stone (13-L-7).
6. *Pits.*—Pitted.
7. *Base.*—Rounded.
8. *Stem scar.*—Apparent but not prominent.
9. *Apex.*—Pointed.
10. *Wing.*—Inner surface — smooth. Ventral surface — Hull thickness 4 mm (0.16 inch).
11. *Percent kernel to nut.*—55%.

Kernel:

1. *Size.*—Length: 23–27 mm (0.91–1.06 inch). Width: 13–14 mm (0.51–0.55 inch).
2. *Form.*—Ovate.
3. *Thickness.*—6–8 mm (0.25–0.31 inch).
4. *Bark.*—Slightly rounded.
5. *Stem scar.*—Not apparent.
6. *Apex.*—Acute.
7. *Surface texture.*—Ribbed similar to 'Nonpareil'.
8. *Perticle.*—a. Thickness — very thin.
9. *Pubescence.*—None.
10. *Color.*—Chevreuse Oakheart + (6-G-10).
11. *Numbers of doubles produced.*—Independent analysis — 0.54%. Examination of over 100 shelled almonds by evaluation — 0.
12. *Flavor.*—Very good.
13. *Quality.*—Good; appropriate for fresh market use. Keeping & Shipping Qualities — Good. Resistance to Disease — Unknown, however with well-sealed shell, minimal insect infestation.

*14. Pollination requirements.*—Texas/Mission Neplus — 'Nonpareil'.

*15. Harvest.*—August 15–20th, a week before 'Nonpareil' almond in the Sacramento Valley.

*16. Weight.*—75 kernels in 4 oz.

*17. Observed characteristics.*—Color slightly darker than 'Nonpareil'.

The above description of this new variety of almond tree is based on the growing conditions prevalent in the Yuba City area of the Sacramento Valley of Northern California; variations of the usual magnitude, such as differences in maturity date and production, may be due to cultural practices including irrigation, fertilization, pruning, fruit thinning and primary climate changes.

What is claimed is:

1. A new and distinct variety of almond tree as described and illustrated which is somewhat similar to 'Nonpareil' (non patented) but distinguished therefrom by producing nuts that mature a week before 'Nonpareil' for harvesting, husking, shelling, and shipping, which further produces a high quality nut of medium size with a good shell, and which has a sweet flavor and is comparatively free of doubled kernels in the shell.

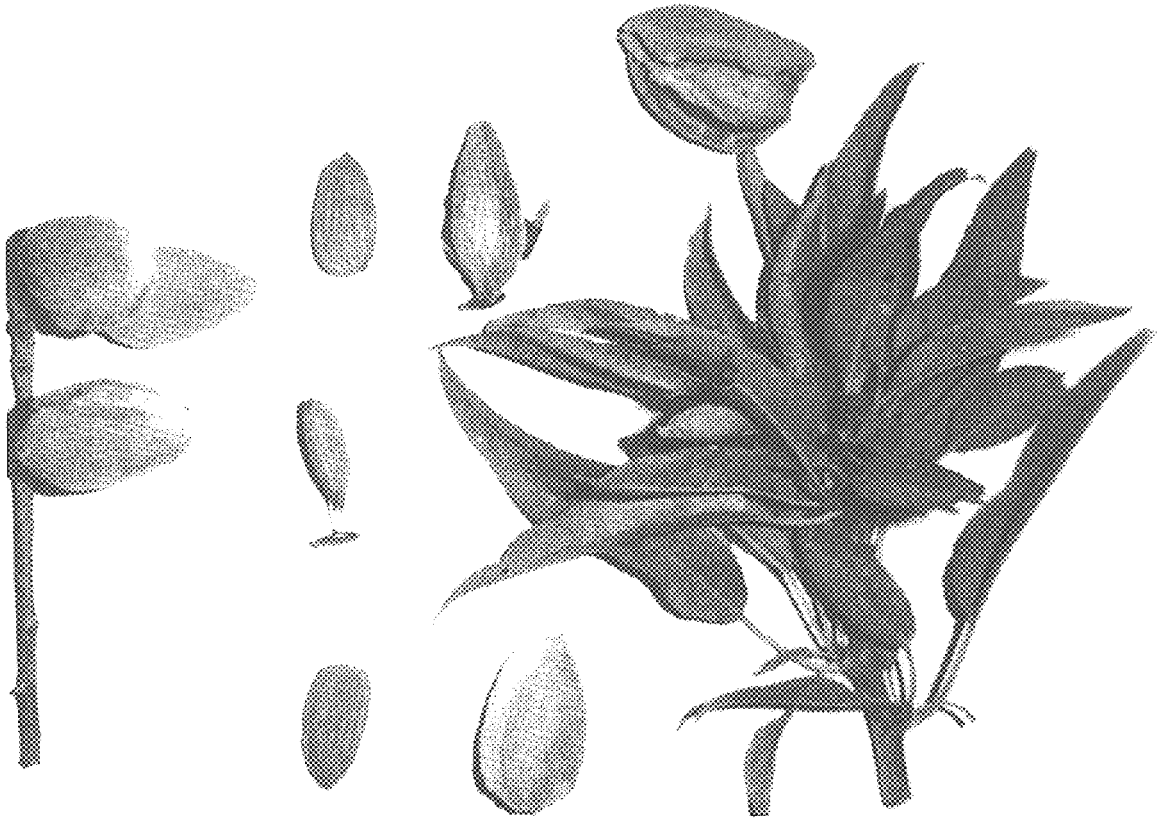

* * * * *